(12) United States Patent
Yokoyama et al.

(10) Patent No.: US 9,822,287 B2
(45) Date of Patent: Nov. 21, 2017

(54) ADHESIVE COMPOSITION AND ENDOSCOPE DEVICE

(71) Applicant: OLYMPUS CORPORATION, Tokyo (JP)

(72) Inventors: Hiroki Yokoyama, Hachioji (JP); Koji Kobayashi, Akiruno (JP); Jun Matsumoto, Hino (JP); Mitsuhiro Nakamura, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 23 days.

(21) Appl. No.: 14/710,986

(22) Filed: May 13, 2015

(65) Prior Publication Data

US 2015/0240137 A1   Aug. 27, 2015

Related U.S. Application Data

(63) Continuation of application No. PCT/JP2014/052508, filed on Feb. 4, 2014.

(30) Foreign Application Priority Data

Apr. 17, 2013  (JP) .................................. 2013-086516

(51) Int. Cl.
    C08G 59/42    (2006.01)
    B32B 18/00    (2006.01)
    B32B 5/16     (2006.01)
    C09J 163/00   (2006.01)
    A61B 1/00     (2006.01)
    G02B 23/24    (2006.01)
    A61B 1/05     (2006.01)

(52) U.S. Cl.
    CPC ........... *C09J 163/00* (2013.01); *A61B 1/0008* (2013.01); *A61B 1/0011* (2013.01); *A61B 1/00064* (2013.01); *A61B 1/051* (2013.01); *G02B 23/2476* (2013.01)

(58) Field of Classification Search
    CPC . A61B 1/00064; A61B 1/0008; A61B 1/0011; A61B 1/051; C09J 163/00; G02B 23/2476
    See application file for complete search history.

(56) References Cited

U.S. PATENT DOCUMENTS

2010/0173164 A1* 7/2010 Yoshida ............... C08G 59/621
                                                              428/414
2012/0082842 A1    4/2012 Hirano et al.

FOREIGN PATENT DOCUMENTS

| CN | 102471661 A | 5/2012 |
|---|---|---|
| JP | 2002-238834 A | 8/2002 |
| JP | 3806635 B2 | 8/2006 |
| JP | 2009-256630 A | 11/2009 |
| JP | 4875790 B2 | 2/2012 |
| WO | WO 2011/126018 A1 | 10/2011 |
| WO | WO 2013/051458 A1 | 4/2013 |

OTHER PUBLICATIONS

Machine translation of JP 2009-256630, Kodama et al, Nov. 5, 2009, p. 1-22.*
Chinese Office Action dated Nov. 19, 2015 from related Chinese Patent Application No. 201480003009.6, together with an English language translation.
English translation of International Preliminary Report on Patentability dated Oct. 29, 2015 together with the Written Opinion received in related International Application No. PCT/JP2014/052508.
Extended Supplementary European Search Report dated Oct. 21, 2016 in related European Patent Application No. 14 78 5596.9.
Japanese Office Action dated Aug. 23, 2016 received in JP 2013-086516.
International Search Report dated Mar. 11, 2014 issued in PCT/JP2014/052508.
English Abstract of JP 2003-126023 A, dated May 7, 2003.
English Abstract of EP 2433996 A1, dated Mar. 28, 2012.

* cited by examiner

*Primary Examiner* — Robert T Butcher
(74) *Attorney, Agent, or Firm* — Scully, Scott, Murphy & Presser, P.C.

(57) ABSTRACT

An adhesive composition comprising a main agent including at least one epoxy resin selected from a bisphenol A epoxy resin, a bisphenol F epoxy resin, and a phenol novolac epoxy resin, and an acrylic rubber; a curing agent including xylylene diamine; and a filler including silica. The adhesive composition further comprises an ion exchanger.

20 Claims, 2 Drawing Sheets

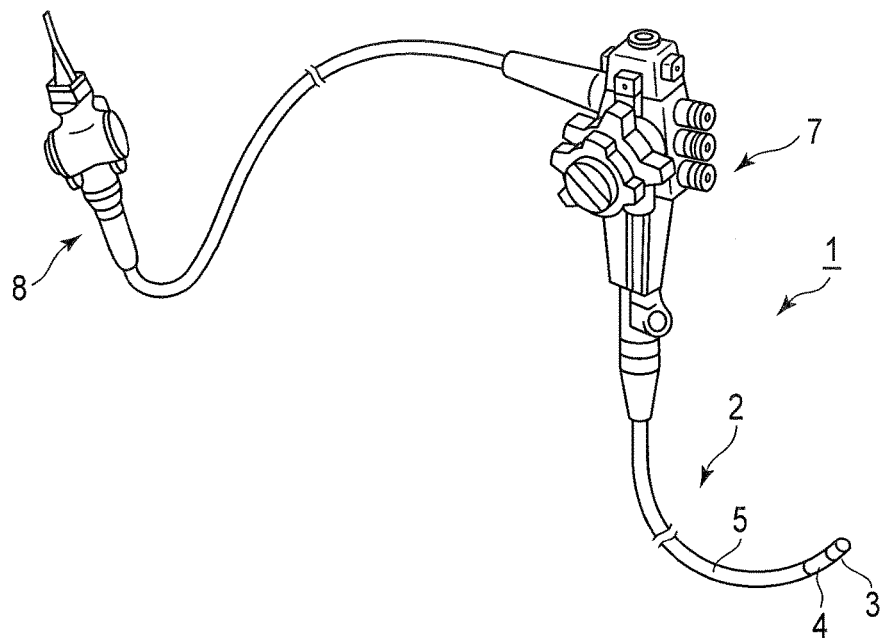
F I G. 1
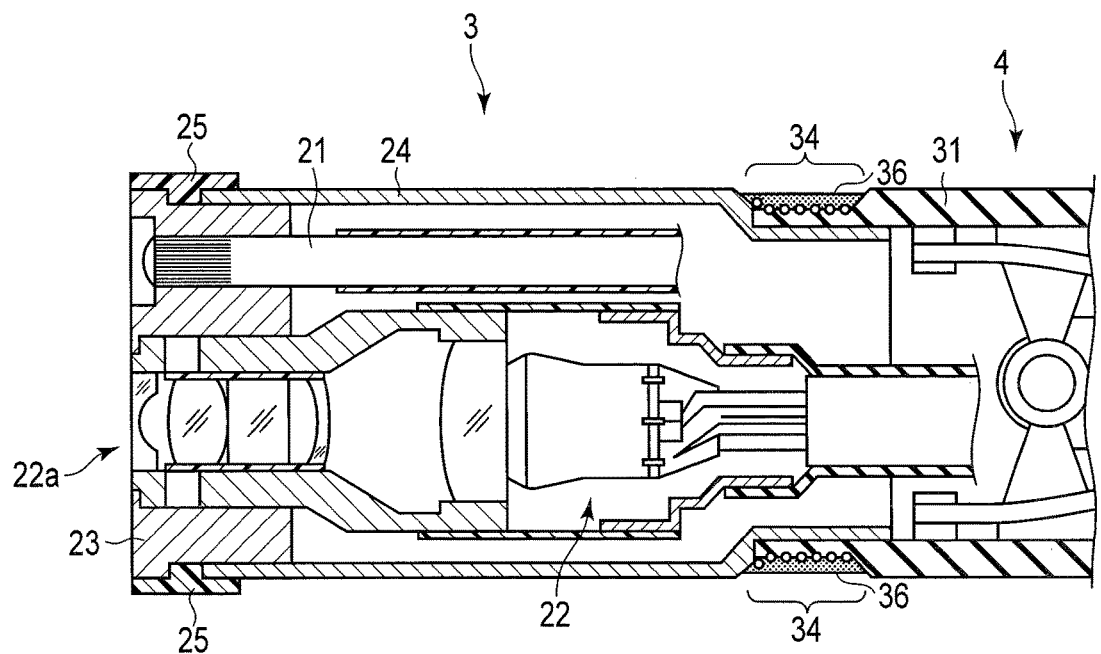
F I G. 2

ADHESIVE COMPOSITION AND ENDOSCOPE DEVICE

CROSS-REFERENCE TO RELATED APPLICATIONS

This application is a Continuation Application of PCT Application No. PCT/JP2014/052508, filed Feb. 4, 2014 and based upon and claiming the benefit of priority from Japanese Patent Application No. 2013-086516, filed Apr. 17, 2013, the entire contents of all of which are incorporated herein by reference.

BACKGROUND OF THE INVENTION

1. Field of the Invention

The present invention relates to an adhesive composition and an endoscope device.

2. Description of the Related Art

It is necessary for an endoscope to make a diameter of a part inserted into a body cavity (insertion part) as narrow as possible for inserting it into the body cavity, or the like. Various items are incorporated inside the insertion part to diversify the functions of the endoscope.

For example, various tubes are incorporated into the insertion part of the endoscope, and an adhesive is used for fixing open parts of the tubes to the tip or an operation part. In addition, an optical system is provided on a hard part of the tip of the insertion part for observing the inside of a body cavity. The optical system includes a cover lens and lenses thereof, and a cover lens and lenses thereof for illumination from a light guide, and an adhesive is used for fixing these lenses on a lens frame or the hard part of the tip.

Within the insertion part are further incorporated a light guide for transmitting light to the tip part, and an image guide for transmitting an image to an eyepiece part. Fiber bundles, in which a number of fibers are bundled, are used for the light guide and the image guide. An adhesive is used for fixing the fiber bundles to the lens frame or the hard part of the tip part.

As regards an electronic endoscope, in addition to the tubes and fiber bundles described above, cables, which transmit electric signals to a connector part from a CCD and the like within the hard part of the tip part, are also incorporated. An adhesive is used for protecting and fixing the CCD and the like.

The adhesive is also used for finishing an outer surface of the endoscope. Prior to the finishing using the adhesive, an edge of a flexible sheath tube is tightly bound with threads from the outside, which is fixed on a member inside thereof. In order to secure an insertion property of the flexible sheath tube and prevent loose threads, an adhesive is coated on the threads. In this way, the finishing of the outer surface and the fixing of the threads are performed.

The endoscope is required to be completely sterilized, because it is inserted into the body cavity of a patient. The endoscope is subjected to a sterilization treatment using an autoclave with high temperature and high pressure steam, or a sterilization treatment using a chemical such as peracetic acid or gas (such as hydrogen peroxide gas or ethylene oxide gas). When a medical device such as an endoscope is subjected to the sterilization treatment using the autoclave or the chemical, the adhesive layer can be deteriorated by saturated steam or the chemical, and thus members bonded by the adhesive may be peeled off from each other.

JP No. 3806635 proposes that deterioration of an adhesive layer is prevented by incorporating predetermined filler in the adhesive to enhance a sterilization resistance even after a sterilization treatment. JP 2002-238834-A discloses that in order to maintain air tightness and durability of a bonded part of lenses and a frame in a bonded lens unit even after a sterilization treatment, the lenses are bonded to the frame using an adhesive containing a thermosetting resin such as an epoxy resin, and a filler. JP No. 4875790 discloses that when certain silica is contained as a filler, an adhesive layer which has sufficient durability against various disinfection methods and which hardly transmits steam can be obtained.

BRIEF SUMMARY OF THE INVENTION

Some of the conventional adhesives, however, have insufficient durability when the sterilization treatment is performed multiple times, and if the sterilization treatment is repetitively performed, the members bonded through the adhesive layer may sometimes be peeled off from each other. In addition, the sterilization treatment may change the color of the adhesive layer, cause cracks in the adhesive layer, or dissolve the adhesive layer, thus resulting in a deteriorated appearance of the adhesive layer in the endoscope outer surface.

When a sterilization treatment using hydrogen peroxide plasma (gas sterilization treatment) is performed, the adhesive layer can be more severely deteriorated. For example, the adhesive layer may be peeled off from a forming member, or the surface of the adhesive layer may change to a foamy state, which reduces the performance.

The present invention has been made in view of the circumstance described above, and aims at providing an adhesive composition capable of forming an adhesive layer, which has excellent sterilization resistance and which can maintain excellent adhesive strength and appearance, even after a sterilization with hydrogen peroxide plasma.

The present invention also aims at providing an endoscope device in which an adhesive layer, which bonds constituent materials to each other or coats the constituent materials, has an excellent sterilization resistance and can maintain excellent adhesive strength and appearance after a sterilization with hydrogen peroxide plasma.

A solution to the problems described above is an adhesive composition comprising a main agent containing at least one epoxy resin selected from a bisphenol A epoxy resin, a bisphenol F epoxy resin, and a phenol novolac epoxy resin, and an acrylic rubber; a curing agent containing xylylene diamine, a filler containing silica; and an ion exchanger.

The ion exchanger can contain at least one substance selected from styrene, derivatives thereof, divinyl benzene, derivatives thereof, bismuth, antimony, zirconium, magnesium, and aluminum.

The ion exchanger may be contained in a content of 0.8 to 12 parts by mass based on 100 parts by mass of the main agent.

The endoscope device, which is one embodiment of the present invention, is characterized in that at least two constituent members are bonded to each other through an adhesive layer obtained by curing the adhesive composition described above.

According to the present invention, an adhesive composition capable of forming an adhesive layer which has excellent sterilization resistance and which can maintain excellent adhesive strength and appearance, even after a sterilization with hydrogen peroxide plasma, is provided.

According to the present invention, an endoscope device in which an adhesive layer bonding constituent materials to each other or coating the constituent materials has excellent sterilization resistance and can maintain excellent adhesive strength and appearance, even after sterilization with hydrogen peroxide plasma, is provided.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a perspective view showing a schematic configuration of an endoscope according to one embodiment.

FIG. 2 is a partial cross-sectional side view of a distal tip part of the endoscope to which outer sheath tube is fixed.

DETAILED DESCRIPTION OF THE EMBODIMENT OF THE INVENTION

Figure 3:
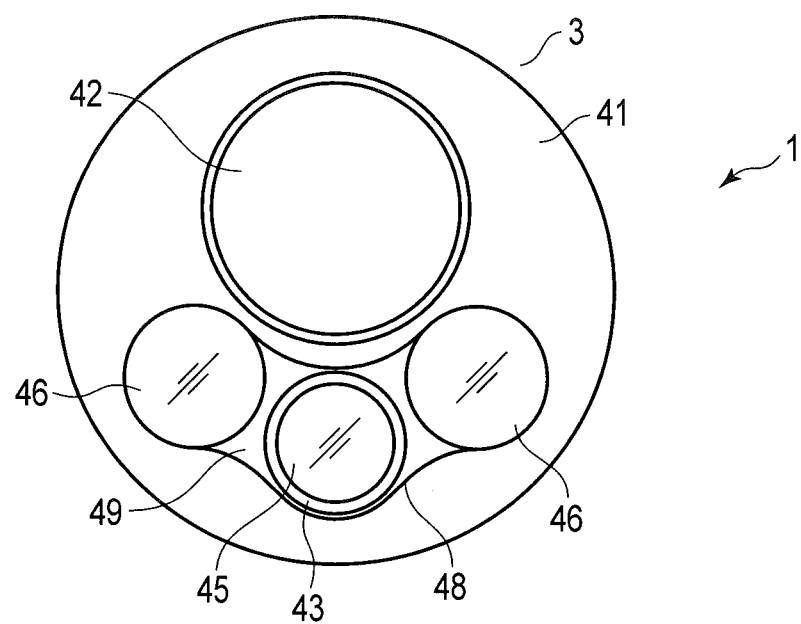
FIG. 3 is a front view of a distal tip part of the endoscope.

Adhesive compositions according to the embodiments of the present invention and endoscope devices using the same will be explained below. The adhesive composition of the present embodiment comprises an ion exchanger in addition to a main agent, a curing agent, and a filler, and is preferably used as an adhesive for a medical device.

The main agent contains an acrylic rubber and an epoxy resin. The acrylic rubber provides moisture resistance and heat resistance capable of standing a sterilization treatment, in particular a sterilization treatment in high temperature and high pressure steam, to the adhesive composition, and plays a role to maintain a good the adhesive strength.

The acrylic rubber is preferably used in a state of a fine powder having an average particle size of 300 nm or less. The acrylic rubber can be used in a state in which the rubber is dispersed in an epoxy resin described below (a bisphenol A epoxy resin, a bisphenol F epoxy resin, or a phenol novolac epoxy resin). When the epoxy resin in which the acrylic rubber is dispersed is heated, a sea-island structure in which the acrylic rubber is distributed like islands in the epoxy resin is formed. As a result, it is easy to exhibit the adhesive properties such as the sterilization resistance even in high temperature and high humidity conditions.

It is generally said that the formation of the sea-island structure has a tendency to depend on the mixing condition or the curing condition of the epoxy resin and the acrylic rubber; however, when the acrylic rubber is dispersed in the epoxy resin, the sea-island structure can be easily formed without depending too much on the mixing condition or curing condition, whereby flexibility in the bonding work or the curing condition can be increased.

The content of the acrylic rubber is preferably from about 1 to 20% by mass of the total amount of the main agent. When the acrylic rubber is contained, the cross-linking density can be increased in addition to the adhesion shear strength and the adhesion peel strength, thus resulting in improved autoclave resistance or chemical resistance of the cured product. As a result, even if the sterilization treatment in high temperature and high pressure steam or the sterilization treatment using the chemical is performed, an adhesive composition capable of exhibiting sufficient adhesive strength can be easily obtained. The content of the acrylic rubber is more preferably from about 5 to 15% by mass of the total amount of the main agent. Specifically, AC-3365 (manufactured by Aika Kogyo Co., Ltd.) and the like can be used as the acrylic rubber.

The epoxy resin in the main agent contains at least one resin selected from bisphenol A epoxy resins, bisphenol F epoxy resins, and phenol novolac epoxy resins.

It is preferable to contain three kinds of epoxy resin, bisphenol A epoxy resin, bisphenol F epoxy resin, and phenol novolac epoxy resin, because the adhesive layer having high sterilization resistance, appropriate viscosity, and high adhesive strength can be obtained, even if the sterilization treatment is repetitively performed.

The content of the bisphenol A epoxy resin is preferably from about 20 to 70 parts by weight, based on 100 parts by mass of the main agent, more preferably from 30 to 60 parts by weight. Specifically, JER 828 (manufactured by Mitsubishi Chemical Corporation) and the like can be used as the bisphenol A epoxy resin.

The content of the bisphenol F epoxy resin is preferably from about 10 to 60 parts by mass, based on 100 parts by mass of the main agent, more preferably about from 30 to 60 parts by mass. Specifically, JER 807 (manufactured by Mitsubishi Chemical Corporation) and the like can be used as the bisphenol F epoxy resin.

The content of the phenol novolac epoxy resin is preferably from about 20 to 40 parts by weight, based on 100 parts by mass of the main agent, more preferably from about 30 parts by weight. Specifically, N-770 (manufactured by DIC Corporation) and the like can be used as the phenol novolac epoxy resin.

Xylylene diamine can be used as the curing agent, and the curing agent may further contain a derivative thereof. The xylylene diamine and the derivative thereof may be called as an "amine-based curing agent." When the derivative thereof is contained together with the xylylene diamine, the reaction speed with the main agent can be increased. The examples of the derivative of the xylylene diamine include alkylene oxide adducts, glycidyl ester adducts, glycidyl ether adducts, Mannich adducts, acrylonitrile adducts, epichlorohydrin adducts, xylylene diamine trimer, and the like.

Meta-Xylylene diamine is preferable, because it has an aromatic backbone and is structurally rigid.

When the xylylene diamine derivative is used, the content thereof is preferably from about 10 to 99% by mass of the total amount of the curing agent, more preferably from about 30 to 97% by mass. When the xylylene diamine and the derivative thereof is contained in the range described above, the appropriate reaction speed can be obtained, and effects of suppression of a reaction with carbonic acid gas in the air and improvement of the adhesive strength can also be obtained.

In addition to the amine-based curing agent as described above, another compound may be contained as the curing agent. The examples of other compound include polyamide resins, imidazoles, acid anhydrides, and the like.

It is desired that the blending ratio of the main agent and the curing agent is adjusted so that the epoxy groups in the epoxy resin in the main agent are equivalent to the functional groups reacting with the epoxy groups in the curing agent.

Regarding the epoxy resin, a molecular weight per function is referred to as an epoxy equivalent, and an amine equivalent of the amine-based curing agent is referred to as an active hydrogen equivalent. A theoretical blending ratio is calculated from the epoxy equivalent and the amine equivalent, and an optimum blending ratio is determined from the adhesive strength, and the like, using the theoretical blending ratio as a guide to an appropriate blending ratio.

The blending ratio (mass ratio) of the main agent to the curing agent is preferably from 10:1 to 10:9. When the main agent and the curing agent are contained in this pre-determined blending ratio, disadvantages such as oxidative deterioration, softening deterioration caused by hydrolysis or heat, curing deterioration, brittle fracture and reduction of the adhesive strength can be avoided. The blending ratio of the main agent to the curing agent is more preferably from 10:1 to 10:7.

The adhesive composition of the present embodiment contains silica as the filler. Silica may be, for example, spherical silica having an average particle size of 4 µm or more and 7 µm or less. The content thereof is preferably from 20 to 40 parts by mass based on 100 parts by mass of the adhesive main agent. Here, the average particle size is a volume-based average particle size, and can be obtained in a usual manner.

The shape of the silica can be determined by observation with an electronic microscope. The silica which can be used includes fused silica such as spherical silica produced by fusing natural quartz crystals with a burner. More specifically, HPS-3500 (manufactured by Toagosei Co., Ltd.) and the like can be used.

The adhesive composition of the present embodiment contains an ion exchanger in addition to the main agent, the curing agent and the filler.

The deterioration of the adhesive layer during the hydrogen peroxide plasma sterilization is caused by the sterilizing gas attacking the adhesive layer, which cuts polymerization parts in the resin forming the adhesive layer. Thus if the sterilizing gas can be trapped, the disadvantage described above can be avoided, and the sterilization resistance can be improved. The present inventors have found that the ion exchanger effectively acts as a material trapping the sterilizing gas.

The ion exchanger is a substance having an ion exchange capability, and it is preferably contained in an amount of 0.8 to 12 parts by mass based on 100 parts by mass of the main agent. When the ion exchanger is contained in an amount of 1 to 5 parts by mass based on 100 parts by mass of the main agent, the adhesive layer having more excellent properties can be formed.

The examples of the ion exchanger include organic ion exchangers containing at least one compound selected from the group consisting of styrene, divinyl benzene, and derivatives thereof. The examples of the organic ion exchanger which can be used, include Amberlite (manufactured by Organodaw Chemical Company), and DIAION AMP 03 (manufactured by Mitsubishi Chemical Corporation), and the like.

As the ion exchanger, an inorganic ion exchanger may be used which contains at least one member selected from bismuth, antimony, zirconium, magnesium, and aluminum as a main component. Specifically, the examples of the inorganic ion exchanger which can be used, include IXE-500 (manufactured by TOAGOSEI Co., Ltd.), and the like.

The adhesive composition of the present embodiment can form the adhesive layer, which has the excellent sterilization resistance and which can maintain excellent adhesive strength and appearance, even if the sterilization treatment using the hydrogen peroxide plasma is performed, because the composition contains the ion exchanger. Moreover, the adhesive composition of the present embodiment has a viscosity appropriate for forming an adhesive layer having no defects, and has a good workability.

The adhesive composition of the present embodiment may contain fumed silica in a content of about 0.1 to 5% of the total mass of the adhesive, in order to increase thixotropy considering the workability.

The adhesive composition of the present embodiment may further contain additives such as a catalyst, an adhesiveness imparting agent, a solvent, a plasticizer, an antioxidant, a polymerization inhibitor, a surfactant, an antifungal agent, and a coloring agent. These additives may be previously added to the main agent, or may be added to a mixture of the main agent and the curing agent.

Using the adhesive composition described above, parts of an endoscope can be bonded to each other, for example, in a method described below.

First, a liquid containing the main agent and a liquid containing the curing agent are mixed in a pre-determined ratio, to which the filler and the ion exchanger are added. Then, the obtained mixture is coated on surfaces of given endoscope parts to be applied using a brush or the like, and the parts are bonded and fixed. After that, the assembly is heated at a pre-determined temperature for a pre-determined time, thereby strongly bonding the endoscope parts to each other.

Sealing of an imaging device of the endoscope, and exterior finishing and fixing of edges of the flexible sheath tube can be performed in the same manner as above. Furthermore, the adhesive layer can be built up around lenses for observation or lenses for illumination in the same manner as above.

The heating temperature varies depending on the kind and the blending ratio of the main agent and the curing agent contained in the adhesive composition, and is preferably about 60 to 135° C. When the heating temperature is within the range described above, the curing reaction can proceed at a practical speed. Moreover, endoscope parts having a low heat resistance are not thermally deteriorated. The heating time is preferably from about 0.5 to 3 hours.

The members bonded using the adhesive composition described above are not particularly limited so long as they are members constituting the endoscope device. For example, using the adhesive composition of the present embodiment, open parts of various tubes, which are incorporated into an insertion part of an endoscope device, can be fixed on a tip part of the insertion part or an operation part. It is also possible to fix lenses, disposed on a hard part in the tip part of the insertion part, on a lens frame or the hard part in the tip part. It is further possible to fix a fiber bundle, which is incorporated in the insertion part, on the lens frame or the hard part in the tip part. The adhesive composition of the present embodiment can also be used for protecting and fixing CCD, which is incorporated in the hard part in the tip part.

When the exterior finishing is performed using the adhesive composition of the present embodiment, the insertion property can be secured. Specifically, the edge of a flexible sheath tube in the insertion part of the endoscope device is tightly bound with threads from the outside, thus, the edge of a flexible sheath tube is fixed on a member inside thereof. The securing of the insertion property by the exterior finishing and the preventing threads from fraying can be attained at the same time by coating the tightly bounded thread with the adhesive composition.

Referring to the drawings, the endoscope device using the adhesive composition of the present embodiment will be explained below.

As shown in FIG. 1, the endoscope device 1 of the present embodiment comprises a thin and long insertion part 2, which is to be inserted into a body of a subject; an operation part 7, which is connected to the insertion part 2; and a universal cord 8, which is electrically connected to the operation part 7 and supplies illumination light.

A tip part 3 at a tip of the insertion part 2 irradiates illumination light from the tip, and receives reflection light from the inside of the body. A bendable part 4 and a flexible tube 5 contain optical fibers transmitting light received at the tip part 3, and can be bent.

In such an endoscope device 1, members to be bonded using the adhesive composition are not particularly limited so long as they are members constituting the endoscope device 1. A use mode in the present embodiment is explained below by examples.

In the tip part 3 of the endoscope device 1, as shown in FIG. 2, a light guide fiber 21, which supplies illumination light, and a hard part 23 in the tip part, which holds an imaging unit 22 and is in the shape of a cylindrical block are provided, and a tip part cover 24 is fitted around a side surface of the hard part 23 in the tip part. An adhesive layer 25 using the adhesive composition described above is provided at a section where the hard part 23 in the tip part and the tip part cover 24 are fitted, and bonds them.

A tubular bendable rubber 31, which covers a periphery of the bendable part 4, is externally fitted at the base end side of the tip part cover 24. Threads are wound around the bendable rubber 31 and tightly bound at the externally fitted part of the bendable rubber 31 to form a thread wound part 34, whereby the bendable rubber 31 is fixed on the tip part cover 24. An adhesive layer 36 using the adhesive composition described above is formed on a periphery of the thread wound part 34, whereby the securing of the insertion property by the exterior finishing and the preventing threads from fraying can be attained at the same time. The adhesive layer 36 covers the thread wound part 34 along the side surfaces of the tip part cover 24 and the bendable rubber 31. When the insertion part 2 is inserted, the tip part 3 and the bendable part 4 come into contact with a living body and can slide smoothly.

In the endoscope device 1, using the adhesive composition described above, open parts of various tubes, which are incorporated into the insertion part 2 of the endoscope device 1, can be fixed on the tip part of the insertion part 2 and the operation part 7. Lenses 22a, disposed on the hard part 23 in the tip part of the insertion part 2, may be fixed on a lens frame or the hard part 23 in the tip part. A fiber bundle, which is incorporated in the insertion part 2, may also be fixed on a lens frame or the hard part 23 in the tip part. Further, CCD of the imaging unit 22, put in the tip part 3, can be provided, fixed and sealed.

A periphery of a connection part of the bendable part 4 and the flexible tube 5, which are not shown in drawings, has the same structure as that of the periphery of the connection part of the tip part 3 and the bendable part 4. Specifically, at the connection part of the bendable part 4 and the flexible tube 5, a thread wound part is formed, and a periphery of the thread wound part is coated with the same adhesive composition as above. when the adhesive layer using such an adhesive composition is provided, the securing of the insertion property by the exterior finishing and the preventing threads from fraying can be attained at the same time.

Imaging elements of the endoscope device can also be sealed using the adhesive composition described above. It is also possible to build up the adhesive composition around lenses for observation or lenses for illumination in the endoscope device to smooth corners of the lens peripheries.

The adhesive composition of the present embodiment may also be disposed around the lens frame in the tip part 3 of the endoscope device 1.

FIG. 3 is a front view of the tip part 3 of the endoscope 1. A forceps channel 42 is provided in an insulating member 41. An objective lens 45 is disposed between two illumination lenses 46, and an adhesive 49 is filled in a space between the illumination lens 46 and a frame 43 for the objective lens to form a partition 48. This structure prevents direct incidence of light from the illumination lens 46 to the objective lens 45, and fixes the illumination lenses 46 and the frame 43 for the objective lens with the adhesive layer 49.

As described above, in the present embodiment, the ion exchanger is blended with the adhesive composition comprising the main agent containing the acrylic rubber and the epoxy resin, the curing agent containing the xylylene diamine and the derivative thereof, and the filler. The epoxy resin is at least one resin selected from the bisphenol A epoxy resins, bisphenol F epoxy resins, and phenol novolac epoxy resin.

When such an adhesive composition is used, it is possible to form the adhesive layer which has the excellent sterilization resistance and which can maintain excellent adhesive strength and appearance, even after a sterilization with the hydrogen peroxide plasma.

Moreover, the adhesive composition of the present embodiment has a viscosity appropriate for bonding members of the endoscope or for work such as exterior finishing. The adhesive composition described above is used for various applications. For example, it is used for bonding parts of the endoscope, exterior finishing of the flexible sheath tube edge in the insertion part of the endoscope and fixing the threads, sealing the imaging elements of the endoscope, or smoothing the corners of the lens periphery by building up the adhesive around lenses for observation or lenses for illumination in the endoscope. It is possible, accordingly, to obtain an endoscope device having an adhesive layer whose sterilization resistance is not deteriorated so much by any disinfection method.

EXAMPLE

Examples of the present invention will be explained below; however, the present invention is not limited to Examples below.

Example 1

A bisphenol A epoxy resin, a phenol novolac epoxy resin, and an acrylic rubber were mixed to prepare a main agent. Amounts (parts by mass) of the components in the main agent are as follows:

Bisphenol A epoxy resin: 70 parts by mass

Phenol novolac epoxy resin: 30 parts by mass

Acrylic rubber particles: 10 parts by mass

The main agent prepared as above and meta-xylylene diamine, which was a curing agent, were mixed in a mass ratio of 10:4, and silica, which was a filler, was added to the obtained mixture. The silica used was spherical fused silica having an average particle size of 6 μm, and the content thereof was 21% by mass of the total amount of the composition.

As an ion exchanger, an organic ion exchanger (Amberlite manufactured by Organodaw Chemical Company) was prepared, and it was added in an amount of 0.8 parts by mass based on 100 parts by mass of the main agent, thereby producing an adhesive composition of Example 1.

Adhesive compositions of Examples 2 to 18 were obtained in the same manner as in Example 1, except that the content of the organic ion exchanger was changed to that shown in Tables 1 and 2 below. Numbers of each component in Tables 1 and 2 express parts by mass of each component.

TABLE 1

| | | Example | | | | | | | | |
|---|---|---|---|---|---|---|---|---|---|---|
| | | 1 | 2 | 3 | 4 | 5 | 6 | 7 | 8 | 9 |
| Main agent | Bisphenol A epoxy resin (JER 828, Mitsubishi Chemical Corporation) | 70 | 70 | 70 | 70 | 70 | 70 | — | — | — |
| | Bisphenol F epoxy resin (JER 807, Mitsubishi Chemical Corporation) | — | — | — | — | — | — | 70 | 70 | 70 |
| | Acryric rubber (AC-3365, Aika Kogyo Co., Ltd.) | 10 | 10 | 10 | 10 | 10 | 10 | 10 | 10 | 10 |
| | Phenol novolac epoxy resin (N-770, DIC Corporation) | 30 | 30 | 30 | 30 | 30 | 30 | 30 | 30 | 30 |
| Curing agent | meta-xylylene diamine (Mitsubishi Gas Chemical Company, Ind.) | 40 | 40 | 40 | 40 | 40 | 40 | 40 | 40 | 40 |
| Filler | Silica (HPS-3500, Toagosei Co., Ltd.) | 40 | 40 | 40 | 40 | 40 | 40 | 40 | 40 | 40 |
| Ion exchanger (Amberlite, Organodaw Chemical Company) | | 0.8 | 1 | 3 | 5 | 10 | 12 | 0.8 | 1 | 3 |

TABLE 2

| | | Example | | | | | | | | |
|---|---|---|---|---|---|---|---|---|---|---|
| | | 10 | 11 | 12 | 13 | 14 | 15 | 16 | 17 | 18 |
| Main agent | Bisphenol A epoxy resin (JER 828, Mitsubishi Chemical Corporation) | — | — | — | 10 | 10 | 10 | 10 | 10 | 10 |
| | Bisphenol F epoxy resin (JER 807, Mitsubishi Chemical Corporation) | 70 | 70 | 70 | 35 | 35 | 35 | 35 | 35 | 35 |
| | Acryric rubber (AC-3365, Aika Kogyo Co., Ltd.) | 10 | 10 | 10 | 35 | 35 | 35 | 35 | 35 | 35 |
| | Phenol novolac epoxy resin (N-770, DIC Corporation) | 30 | 30 | 30 | 30 | 30 | 30 | 30 | 30 | 30 |
| Curing agent | meta-xylylene diamine (Mitsubishi Gas Chemical Company, Ind.) | 40 | 40 | 40 | 40 | 40 | 40 | 40 | 40 | 40 |
| Filler | Silica (HPS-3500, Toagosei Co., Ltd.) | 40 | 40 | 40 | 40 | 40 | 40 | 40 | 40 | 40 |
| Ion exchanger (Amberlite, Organodaw Chemical Company) | | 5 | 10 | 12 | 0.8 | 1 | 3 | 5 | 10 | 12 |

Adhesive compositions of Comparative Examples 1 to 3 were obtained in the same manner as in Example 1, except that the composition was changed to that shown in Table 3 below. Numbers in each component in Table 3 express parts by mass of each component.

TABLE 3

| | | Comparative Example | | |
|---|---|---|---|---|
| | | 1 | 2 | 3 |
| Main agent | Bisphenol A epoxy resin (JER 828, Mitsubishi Chemical Corporation) | 70 | — | 10 |
| | Bisphenol F epoxy resin (JER 807, Mitsubishi Chemical Corporation) | — | 70 | 35 |
| | Acryric rubber (AC-3365, Aika Kogyo Co., Ltd.) | 10 | 10 | 35 |
| | Phenol novolac epoxy resin (N-770, DIC Corporation) | 30 | 30 | 30 |
| Curing agent | meta-xylylene diamine (Mitsubishi Gas Chemical Company, Ind.) | 40 | 40 | 40 |
| Filler | Silica (HPS-3500, Toagosei Co., Ltd.) | 40 | 40 | 40 |
| Ion exchanger (Amberlite, Organodaw Chemical Company) | | — | — | — |

A viscosity of each of the adhesive compositions of Examples 1 to 18 and Comparative Examples 1 to 3 was determined at 25° C. and the workability was evaluated based on the viscosity in accordance with the criteria described below. The smaller the viscosity, the better the workability, but the workability is good with no problem when the viscosity is 200 Pa·s or lower.

A: Lower than 100 Pa·s
B: 100 Pa·s or higher and 200 Pa·s or lower

An adhesive layer was formed from each resin composition by heating stainless steel test pieces at 80° C. for 2 hours to cure the resin composition. A tensile shearing strength was determined using the test pieces bonded to obtain an SUS-SUS adhesive strength at the initial stage. The tensile shearing strength was measured in accordance with JIS K 6850 [Test method for tensile shearing adhesive strength of adhesives].

The stainless steel test pieces bonded were put in a low temperature plasma sterilization apparatus, and a sterilization treatment was performed using hydrogen peroxide plasma. After that, the test described above was performed to obtain an SUS-SUS adhesive strength after the gas sterilization. When the adhesive strength was 10 MPa or more even after the gas sterilization treatment, it was considered a pass grade (good). When the adhesive strength was less than 10 MPa after the gas sterilization treatment, it was considered inferior.

The appearance of the adhesive layer was visually observed after the gas sterilization, and evaluation was made in accordance with the criteria described below:

A: No change in the appearance (excellent)
B: No bubbles or cracks were generated, but gloss was reduced on the surface (good)

C: A number of bubbles or cracks were generated (inferior)

The obtained results of the workability and the adhesive strengths before and after the sterilization are summarized in Tables 4, 5 and 6 together with an overall evaluation. The overall evaluation was performed in accordance with the criteria described below according to the workability, the adhesive strengths before and after gas sterilization, and the appearance.

A: All items were excellent.
B: The workability or the appearance after the sterilization was "B".
C: Both of the adhesive strength and the appearance were inferior.

TABLE 4

| | | Example | | | | | | | | |
|---|---|---|---|---|---|---|---|---|---|---|
| | | 1 | 2 | 3 | 4 | 5 | 6 | 7 | 8 | 9 |
| Workability | | A | A | A | A | B | B | A | A | A |
| SUS-SUS adhesive strength (MPa) | at initial stage | 20 | 21 | 19 | 19 | 18 | 17 | 20 | 20 | 20 |
| | after gas sterilization | 10 | 15 | 16 | 16 | 12 | 13 | 10 | 15 | 16 |
| Appearance after gas sterilization | | B | A | A | A | A | A | B | A | A |
| Overall evaluation | | B | A | A | A | B | B | B | A | A |

TABLE 5

| | | Example | | | | | | | | |
|---|---|---|---|---|---|---|---|---|---|---|
| | | 10 | 11 | 12 | 13 | 14 | 15 | 16 | 17 | 18 |
| Workability | | A | B | B | A | A | A | A | B | B |
| SUS-SUS adhesive strength (MPa) | at initial stage | 19 | 18 | 17 | 20 | 20 | 22 | 19 | 18 | 17 |
| | after gas sterilization | 16 | 12 | 13 | 10 | 15 | 16 | 16 | 12 | 13 |
| Appearance after gas sterilization | | A | A | A | B | A | A | A | A | A |
| Overall evaluation | | A | B | B | B | A | A | A | B | B |

TABLE 6

| | | Comparative Example | | |
|---|---|---|---|---|
| | | 1 | 2 | 3 |
| Workability | | A | A | A |
| SUS-SUS adhesive strength (MPa) | at initial stage | 19 | 18 | 21 |
| | after gas sterilization | 4 | 3 | 5 |
| Appearance after gas sterilization | | C | C | C |
| Overall evaluation | | C | C | C |

As shown in Tables 4 and 5 above, when the adhesive composition containing the ion exchanger was used (Examples 1 to 18), the adhesive strength reached the pass level for all compositions after the gas sterilization. Moreover, all of the adhesive compositions of Examples had the excellent workability. In particular, it is known that in the case of the adhesive compositions containing the ion exchanger in the range of 1 to 5 parts by mass based on 100 parts by mass of the main agent (Examples 2 to 4, 8 to 10, and 14 to 16), the adhesive layer having a particularly excellent overall evaluation can be obtained, and workability of the adhesive composition is extremely excellent.

On the contrary, in the case of containing no ion exchanger (Comparative Examples 1 to 3), as shown in Table 6 above, the adhesive strength after the gas sterilization is remarkably low, such as 3 to 5 MPa. This is caused because gas cannot be trapped during the gas sterilization because of the absence of the ion exchanger, the thus the adhesive layer is damaged by the sterilizing gas.

The adhesive composition containing no ion exchanger cannot form the adhesive layer which has the excellent sterilization resistance and which maintains excellent adhesive strength or appearance after the hydrogen peroxide plasma sterilization; that is, it was confirmed that if the ion exchanger is not contained, the object of the present invention cannot be attained.

Each of the adhesive compositions of Examples 1 to 18 and Comparative Examples 1 to 3 were coated on parts of an endoscope device, and a curing reaction was performed at 80° C. for 2 hours in the state in which the parts were bonded to each other.

An edge of a flexible sheath tube, which was a part of the endoscope, in an insertion part, was tightly bound with threads from the outside and was fixed on a member inside thereof. Then, the tread was coated with the adhesive composition described above, thereby carrying out exterior finishing. An imaging device of the endoscope device was sealed using the adhesive composition.

An adhesive layer was formed by building up the adhesive composition around lenses for observation or lenses for illumination of the endoscope device, whereby the corners of the peripheries of the observation lens and the illumination lens were smoothed. As described above, the assembly operation of the endoscope device could be performed with no problem.

The obtained endoscope device was subjected to the same sterilization treatment using hydrogen peroxide plasma as above, and the adhesive strength and the appearance of the adhesive layer after the sterilization treatment were determined. As a result, no change in the appearance of the adhesive layer was observed after the gas sterilization, and the adhesive strength was excellent.

The present invention is not limited to the Examples above, and it can be carried out in various modifications without departing from the scope of the invention.

According to the explanation described above, an example in which the endoscope device is used as a medical device to which the adhesive composition is applied is used, but the medical device is not particularly limited so long as it is a device which is used by bringing it into contact with a living body or inserting it into the body. The medical device may include, for example, an endoscope device, various devices for surgery, a cell extracting device, a blood component separation device, a blood transfusion device, and the like.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An adhesive composition comprising:
   a main agent comprising an acrylic rubber and an epoxy resin, wherein the epoxy resin is selected from the group consisting of a bisphenol A epoxy resin, a bisphenol F epoxy resin, and a phenol novolac epoxy resin, and combinations thereof;
   a curing agent containing xylylene diamine;

a filler containing silica; and an organic ion exchanger comprising at least one of styrene, divinyl benzene, and derivatives thereof.

2. The adhesive composition according to claim 1, wherein the organic ion exchanger is contained in a content of 0.8 to 12 parts by mass based on 100 parts by mass of the main agent.

3. An endoscope device comprising at least two constituent members bonded to each other through an adhesive layer obtained by curing an adhesive composition according to claim 1.

4. An endoscope device comprising at least two constituent members bonded to each other through an adhesive layer obtained by curing an adhesive composition according to claim 2.

5. The adhesive composition according to claim 1, wherein the acrylic rubber has an average particle size of 300 nm or less.

6. The adhesive composition according to claim 1, wherein the acrylic rubber is contained in a content of about 1 to 20 parts by mass based on 100 parts by mass of the main agent.

7. The adhesive composition according to claim 1, wherein the acrylic rubber is contained in a content of about 5 to 15 parts by mass based on 100 parts by mass of the main agent.

8. The adhesive composition according to claim 1, wherein the epoxy resin is selected from the group consisting of bisphenol A epoxy resin, bisphenol F epoxy resin, and phenol novolac epoxy resin.

9. The adhesive composition according to claim 1, wherein the bisphenol A epoxy resin is contained in a content of about 20 to 70 parts by weight, based on 100 parts by mass of the main agent.

10. The adhesive composition according to claim 1, wherein the bisphenol A epoxy resin is contained in a content of 30 to 60 parts by weight, based on 100 parts by mass of the main agent.

11. The adhesive composition according to claim 1, wherein the bisphenol F epoxy resin is contained in a content of about 10 to 60 parts by weight, based on 100 parts by mass of the main agent.

12. The adhesive composition according to claim 1, wherein the bisphenol F epoxy resin is contained in a content of about 30 to 60 parts by weight, based on 100 parts by mass of the main agent.

13. The adhesive composition according to claim 1, wherein the phenol novolac epoxy resin is contained in a content of about 20 to 40 parts by weight, based on 100 parts by mass of the main agent.

14. The adhesive composition according to claim 1, wherein the phenol novolac epoxy resin is contained in a content of about 30 parts by weight, based on 100 parts by mass of the main agent.

15. The adhesive composition according to claim 1, wherein the xylylene diamine is contained in a content of about 10 to 99% by mass of the total amount of the curing agent.

16. The adhesive composition according to claim 1, wherein the xylylene diamine is contained in a content of about 30 to 97% by mass of the total amount of the curing agent.

17. The adhesive composition according to claim 1, wherein the curing agent further comprises a derivative of xylylene diamine.

18. The adhesive composition according to claim 17, wherein the derivative of xylylene diamine is selected from the group consisting of alkylene oxide adducts, glycidyl ester adducts, glycidyl ether adducts, Mannich adducts, acrylonitrile adducts, epichlorohydrin adducts and xylylene diamine trimer.

19. The adhesive composition according to claim 1, wherein the silica is spherical silica of an average particle size of 4 μm to 7 μm.

20. The adhesive composition according to claim 1, wherein the silica is contained in a content of 20 to 40 parts by mass, based on 100 parts by mass of the adhesive main agent.

* * * * *